United States Patent [19]

Madappally et al.

[11] 4,241,179
[45] Dec. 23, 1980

[54] METHOD FOR DETERMINING A TRANSAMINASE IN A BIOLOGICAL FLUID AND REAGENT COMBINATION FOR USE IN THE METHOD

[75] Inventors: Mathew M. Madappally, Cooper City, Fla.; Giovanni Bucolo, Cupertino, Calif.

[73] Assignee: Coulter Electronics, Inc., Hialeah, Fla.

[21] Appl. No.: 933,183

[22] Filed: Aug. 14, 1978

[51] Int. Cl.$^3$ .................... C12Q 1/52; C12Q 1/32
[52] U.S. Cl. ........................ 435/16; 435/26; 435/810
[58] Field of Search .................. 195/99, 103.5 R; 435/14, 18, 16, 22, 25, 26, 810

[56] References Cited

U.S. PATENT DOCUMENTS

| | | | |
|---|---|---|---|
| 3,956,069 | 5/1976 | Allain et al. | 435/14 |
| 3,985,621 | 10/1976 | Maruyama et al. | 195/103.5 R |
| 4,019,961 | 4/1977 | Klose et al. | 195/103.5 R |
| 4,024,021 | 5/1977 | Strauropoulos et al. | 195/103.5 R |
| 4,086,142 | 4/1978 | Huang et al. | 195/103.5 R |

*Primary Examiner*—Thomas G. Wiseman
*Attorney, Agent, or Firm*—Silverman, Cass & Singer, Ltd.

[57] ABSTRACT

An improvement in a method for determining glutamate oxalacetate transaminase or glutamate pyruvate transaminase present in a biological fluid, in which method L-glutamate is produced from alpha-ketoglutarate by transamination in the presence of the transaminase in the fluid, and the L-glutamate is oxidatively deaminated in the presence of glutamate dehydrogenase with the simultaneous production of reduced beta-nicotinamide adenine dinucleotide in an amount proportional to the content of the transaminase in the fluid, such fluid also containing an endogenous substance which is oxidized in the presence of glutamate dehydrogenase with the simultaneous production of reduced beta-nicotinamide adenine dinucleotide, thereby interfering with the determination. The improvement for obviating the interference caused by the endogenous substance includes oxidizing the endogenous substance in the presence of glutamate dehydrogenase with the simultaneous reduction of beta-nicotinamide adenine dinucleotide, oxidizing the reduced beta-nicotinamide adenine dinucleotide in the presence of lactate dehydrogenase with the simultaneous reduction of pyruvate to lactate, thereafter inhibiting the lactate dehydrogenase activity, and thereafter producing a quantity of L-glutamate from alpha-ketoglutarate by the aforesaid transamination for oxidative deamination thereof and simultaneous production of reduced beta-nicotinamide adenine dinucleotide in an amount proportional to the content of the transaminase in the fluid. A reagent combination is employed for the determination.

22 Claims, No Drawings

METHOD FOR DETERMINING A TRANSAMINASE IN A BIOLOGICAL FLUID AND REAGENT COMBINATION FOR USE IN THE METHOD

BACKGROUND OF THE INVENTION

This invention relates to a method for the quantitative determination or assay of glutamate oxalacetate transaminase or glutamate pyruvate transaminase present in a biological fluid, especially in human blood serum. More particularly, the invention relates to a method in which L-glutamate produced by transamination in the course of the determination is oxidatively deaminated in an oxidation-reduction reaction with simultaneous production of reduced beta-nicotinamide adenine dinucleotide in an amount proportional to the content of the transaminase in the fluid, and to an improvement for obviating the interference caused by another substance in the fluid which while not related quantitatively to the substance being determined undergoes an oxidation-reduction reaction with the production of reduced beta-nicotinamide adenine dinucleotide and thus reduces the accuracy of the determination. The invention also relates to a reagent combination for use in the method.

The activities of the enzymes glutamate oxalacetate transaminase (GOT), also known as aspartate aminotransferase, and glutamate pyruvate transaminase (GPT), also known as alanine aminotransferase, in biological fluids in the past have been determined by the indirect measurement of one of the products of a transamination reaction catalyzed by the transaminase to be determined. A method having certain advantages embodies the production of L-glutamate from alpha-ketoglutarate (2-oxoglutarate) by transamination. The alpha-ketoglutarate is reacted with L-aspartate in the determination of GOT, and with L-alanine in the determination of GPT. In an oxidation-reduction reaction of the L-glutamate with beta-nicotinamide adenine dinucleotide in its oxidized form (NAD), conducted in the presence of the enzyme glutamate dehydrogenase (GLDH) as catalyst, the L-glutamate is oxidatively deaminated, and the NAD is converted to the reduced form (NADH) of the compound. The quantity of NADH produced is proportional to the activity of the transaminase in the biological fluid. The NADH is reacted with 2-p-iodophenyl-3-p-nitrophenyl-5-phenyl tetrazolium chloride (INT) in an oxidation-reduction reaction, to produce the reduced form (INTH) of the latter compound, proportionally to the activity of the transaminase in the fluid. The INTH may be determined quantitatively by measurement of light absorption, preferably at the absorption maximum of 500 nanometers (nm.). The color is very stable and intense, therefore sensitive, and the absorbance is proportional to the concentration of GOT or GPT in the fluid over a large dynamic range.

The foregoing reactions, which have been performed as coupled reactions by incubation of the biological fluid with a single mixed reagent, may be represented as follows:

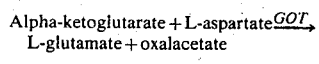

Alpha-ketoglutarate + L-aspartate
L-glutamate + oxalacetate    (1A.)

or

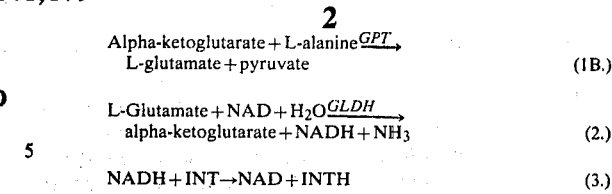

where:
- GOT = Glutamate oxalacetate transaminase
- GPT = Glutamate pyruvate transaminase
- GLDH = Glutamate dehydrogenase
- NAD = Beta-nicotinamide adenine dinucleotide
- NADH = Reduced form of NAD
- INT = 2-p-Iodophenyl-3-p-nitrophenyl-5-phenyl tetrazolium chloride
- INTH = Reduced form of INT Reaction 3 may be catalyzed non-enzymatically, by N-methyl phenazonium methosulfate (PMS—also called phenazine methosulfate), or enzymatically, by diaphorase. The use of diaphorase is preferred, as diaphorase catalyzes the reaction more rapidly, is not affected by light, and is not auto-oxidizable as is PMS. The use of diaphorase also is adaptable to making kinetic measurements of the transaminase activity by following the rate of INTH color formation with time.

While the foregoing method is advantageous, the biological fluids contain endogenous materials which participate in enzymatic oxidation-reduction reactions with the formation of NADH, thereby interfering with the determination. The equilibrium of reaction 2 lies toward the formation of L-glutamate at the reaction pH of about 7–8. Consequently, large concentrations of GLDH are required in order to obtain results which are linear in respect to the concentration of GOT or GPT present. In the presence of large concentrations of GLDH, certain amino acids in the fluids undergo oxidative reactions which result in equivalent production of NADH, owing to the low specificity of the enzyme GLDH. The non-specific NADH produced from such amino acids results in non-specific color due to resulting INTH production and a false elevation of the transaminase activity in the biological fluid. Owing to the high degree of variability in amino acid content of different fluid samples, the false elevation is unpredictable and renders many of the determinations by this procedure valueless.

Also present in biological fluids, particularly serum, are lactate and the enzyme lactate dehydrogenase (LDH), in variable concentrations. Owing to the activity of the enzyme, these substances increase the content of NADH in the assay medium. In the past, oxamate or oxalate has been added to the medium, to inhibit lactate dehydrogenase.

Several other procedures are available to increase the reliability of results obtained with biological fluids containing interfering endogenous substances. Thus, a blank determination can be run for each sample of the fluid, using a reagent which omits the alpha-ketoglutarate. This procedure substantially increases the cost in labor and reagent material. The determination may be preceded by removing L-glutamate from the fluid, with the enzyme glutamate decarboxylase. However, this enzyme does not remove other substances which also are substrates for GLDH. Another mehod which may, to a point, correct for the non-specific color resulting from the oxidation of endogenous substances would be to take readings at two different times, rendering the determination a kinetic one. This procedure would not lend itself conveniently to performance of the determination in automated instruments.

SUMMARY OF THE INVENTION

The invention provides an improvement in a method for determining glutamate oxalacetate transaminase or glutamate pyruvate transaminase present in a biological fluid, preferably human blood serum, wherein L-glutamate is produced from alphta-ketoglutarate by transamination in the presence of the transaminase in the fluid, and the L-glutamate is oxidatively deaminated in the presence of glutamate dehydrogenase with the simultaneous production of reduced beta-nicotinamide adenine dinucleotide in an amount proportional to the content of the transaminase in the fluid, such fluid also containing an endogenous substance which is oxidized in the presence of glutamate dehydrogenase with the simultaneous production of reduced beta-nicotinamide adenine dinucleotide, thereby interfering with the determination. The improvement comprises oxidizing the endogenous substance in the presence of glutamate dehydrogenase with the simultaneous reduction of beta-nicotinamide adenine dinucleotide, oxidizing the resulting reduced beta-nicotinamide adenine dinucleotide in the presence of lactate dehydrogenase with the simultaneous reduction of pyruvate to lactate, thereafter inhibiting the lactate dehydrogenase activity, and thereafter producing a quantity of L-glutamate from alpha-ketoglutarate by said transamination for said oxidative deamination thereof and simultaneous production of reduced beta-nicotinamide adenine dinucleotide in an amount proportional to the content of said transaminase in the fluid.

The invention also provides a new and improved reagent combination for use in the foregoing determination. A first reagent is provided for admixture with the fluid initially, for carrying out the oxidation of the endogenous substance and oxidizing the resulting reduced beta-nicotinamide adenine dinucleotide. A second reagent is provided for admixture with the product resulting from reaction with the first reagent, for inhibiting the lactate dehydrogenase activity and then producing a quantity of L-glutamate by transamination in the presence of the transaminase in the fluid, from which 2-p-iodophenyl-3-p-nitrophenyl-5-phenyl tetrazolium chloride in reduced form is produced in an amount proportional to the content of the transaminase in the fluid.

The improved method eliminates the color development due to non-specific reactions of glutamate dehydrogenase in the presence of beta-nicotinamide adenine dinucleotide with endogenous amino acids in the biological fluid, while eliminating the reaction of both added and endogenous lactate dehydrogenase, thereby materially increasing the accuracy of the determination. Lag phases, common to coupled or multiple-step enzymatic reactions, are reduced by the optimization of components and conditions.

The method is sensitive, requiring only a very small portion of the biological fluid for the assay. A determination can be performed rapidly using common laboratory equipment, and in a single vessel, such as a laboratory tube. The determination may be performed with a single point calibration.

DESCRIPTION OF THE PREFERRED EMBODIMENTS

In the determination of a transaminase in a biological fluid in accordance with the invention, an interfering endogenous amino acid is removed from the fluid or consumed by oxidation of the amino acid with simultaneous reduction of NAD to NADH. The reaction may be represented as follows:

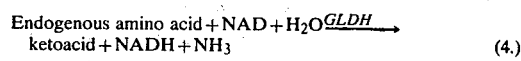

Interfering amino acids found in blood serum include glutamic acid, leucine, isoleucine, valine, methionine, and alpha-aminobutyric acid. Reaction 4 basically is the same as reaction 2. The NADH next is returned to its oxidized state, to prevent interference with the determination as subsequently completed, by the following reaction:

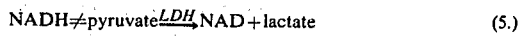

where LDH = Lactate dehydrogenase.

Reactions 4 and 5 are conducted as coupled reactions in a first phase of the determination, with the addition to the fluid of a single reagent, described hereinafter.

Lactate dehydrogenase enzyme, including added and endogenous enzyme, then is inhibited or inactivated, to prevent interference with the following part of the determination. Under the conditions of the determination, particularly at the pH provided in the reaction mixture, the enzyme may be inhibited by the addition of the anions of oxamic acid and oxalic acid. Oxamate serves to inhibit LDH activity in the forward direction, to the right in reaction 5, and oxalate serves to inhibit LDH activity in the reverse direction, to the left in reaction 5.

Following the inhibition of the enzyme LDH, the determination of the transaminase may be carried out without interference caused by the endogenous substances, by conducting reactions 1A or 1B, 2 and 3 as coupled reactions. Reaction 3 preferably is catalyzed by diaphorase. The enzyme inhibition and the latter reactions are conducted in a second phase of the determination, with the addition to the reaction mixture of a single reagent, described hereinafter.

Enzymatic activity is terminated at a predetermined time by acidification, preferably with dilute hydrochloric acid. The absorbance of the reaction product at 500 nm. is measured, and the GOT or GPT activity is calculated therefrom by comparing with the absorbance of a calibrator of known GOT or GPT activity. Alternatively, the enzymatic activity may be maintained, and the rate of change of absorbance at 500 nm. over a period of time is followed and the activity is calculated based upon the molar extinction coefficient of reduced INT.

Reaction 1B has been coupled with reaction 5 in a prior method for the determination of GPT. Reaction 5 is followed by a decrease in absorbance at 340 nm., which is directly proportional to the GPT activity. This method, however, cannot be performed readily on instruments not equipped for continuous measurements at 340 nm., and it may not be suitable for large numbers of assays.

In a preferred procedure, the biological fluid, such as human blood serum, is admixed and incubated successively with two principal reagents. The first reagent contains at least the materials required for conducting reactions 4 (which is the same as reaction 2) and 5, as well as oxidation of any other oxidizable interfering endogenous substance. Thus, the first reagent contains NAD, GLDH, pyruvate, and LDH. The second reagent contains at least the materials required for inhibiting the enzymatic activity of the LDH. In particular, the second reagent contains oxamate and oxalate.

Either reagent may contain the remaining materials required for conducting reactions 1A or 1B. Thus, each of L-aspartate or L-alanine, and alpha-ketoglutarate, may be incorporated in either of the reagents. It is necessary, however, to incorporate the diaphorase and the INT in different reagents, to prevent diaphorase reaction prior to inhibition of LDH activity as well as to prevent possible side-reaction on long standing. If alpha-ketoglutarate and L-aspartate and L-alanine are incorporated together in the first reagent, reactions 1A or 1B and 2 will take place together with reactions 4 and 5. While this procedure may be employed if desired, it is preferred to incorporate the alpha-ketoglutarate, on one hand, and the L-aspartate or L-alanine, on the other hand, in different reagents. Reactions 1A or 1B and 2 then are conducted only after the addition of the second reagent.

The reagents are employed in aqueous solutions of water-soluble reagent materials in distilled or deionized water. Each reagent solution preferably has a pH in the range of about 7.3–8. In general, reagent materials which are derived from acids may be employed in the free acid or a water-soluble salt form, so long as the pH of the reagent and the concentration of the reacting anion stays constant, except that cations should not be present which would inhibit or interfere with the enzymes involved in the reactions. The salts, especially the alkali metal salts, generally are the preferred forms for incorporation in the reagent solutions, for reasons of stability in storage and solubility in the solutions.

The pH is adjusted and maintained by a buffer, which may be one of the phosphate and non-phosphate buffers known to be suitable for the purpose. The preferred buffers include phosphate buffers, "Tris" (tris (hydroxymethyl) aminomethane), and "Tricine" (N-tris (hydroxymethyl) methyl-2-aminoethanesulfonic acid). Preferably, an alkali metal phosphate buffer is employed. In such case, the desired pH is obtained by providing monobasic and dibasic phosphate salts in a suitable ratio, e.g., by titrating a solution of monobasic phosphate against a solution of diabasic phosphate to the desired pH. Alternatively, the buffer may be prepared by adding a strong alkali such as potassium or sodium hydroxide to phosphoric acid solution, to provide the desired pH.

Adenosine-5'-diphosphate is included in the first reagent as a stabilizer for GLDH, and also to increase the specificity of GLDH toward L-glutamate while decreasing the activity of the GLDH toward other amino acids, particularly alanine. A surfactant preferably is added to either of the first and second reagents, to keep the INTH in solution and stabilize the color provided thereby. Surfactants which may be employed include water-soluble cholesterol (Solulan C-24), polyoxyethylene (20) sorbitan monooleate (Tween 20), and polyoxyethylene (50) stearate (Myrj).

Table 1 sets forth a composition preferably employed as the first reagent, together with the relative proportions of the materials. Table 2 similarly sets forth a composition which is preferably employed as the second reagent. The reagents are employed in aqueous solutions of the materials, present in the amounts set forth per liter of solution.

Table 1

| Material | Amount |
| --- | --- |
| Alkali metal L-aspartate or | 100–200 millimoles |
| L-Alanine | 150–300 millimoles |
| Alkali metal pyruvate | 0.25–1 millimole |
| Alkali metal adenosine-5'-diphosphate | 1–5 millimoles |
| Alkali metal phosphate, Tris, or Tricine buffer, pH 7.3–8 | 25–150 millimoles |
| Beta-nicotinamide adenine dinucleotide | 2–5 millimoles |
| Glutamate dehydrogenase | 40–80 I.U. × $10^3$ |
| Lactate dehydrogenase | 0.2–0.5 I.U. × $10^3$ |
| Diaphorase | 1–3 I.U. × $10^3$ |
| Surfactant | 10–30 grams |

The surfactant is one of those identified above. The aspartate is included for the determination of GOT, and the alanine is included for the determination of GPT.

Table 2

| Material | Amount |
| --- | --- |
| Alkali metal alpha-ketoglutarate | 10–50 millimoles |
| Alkali metal oxalate | 25–75 millimoles |
| Alkali metal oxamate | 10–30 millimoles |
| Aklali metal phosphate, Tris, or Tricine buffer, pH 7.3–8 | 25–150 millimoles |
| 2-p-Iodophenyl-3-p-nitrophenyl-5-phenyl tetrazolium chloride | 0.2–1 millimole |

The following example illustrates compositions and procedures for making transaminase determinations in accordance with preferred embodiments of the invention. It will be understood that the invention is not limited to the materials, proportions, conditions and procedures set forth in the example, which are merely illustrative.

EXAMPLE

Transaminase activity in human blood serum is determined employing first and second reagent solutions. The first solution has a pH of about 7.4±0.1 and contains the materials set forth in Table 3 dissolved in distilled or deionized water in the proportions indicated. The aspartate is included in the solution when GOT is to be determined, and the alanine is included in the solution when GPT is to be determined.

Table 3

| Material | Amount Per Liter |
| --- | --- |
| Potassium L-aspartate or | 125 millimoles |
| L-Alanine | 180 millimoles |
| Sodium pyruvate | 0.25 millimoles |
| Sodium adenosine-5'-diphosphate, monohydrate | 2.5 millimoles |
| ($KH_2PO_4$ anhydrous) | |
| ($K_2HPO_4$, anhydrous) | 100 millimoles |
| Beta-nicotinamide adenine dinucleotide (90% pure) | 2.25 millimoles |
| Glutamate dehydrogenase | 60 I.U. × $10^3$ |
| Lactate dehydrogenase | 0.25 I.U. × $10^3$ |
| Diaphorase | 1.75 I.U. × $10^3$ |
| Water soluble cholesterol (Solulan C-24) | 20 grams |

The phosphate salts are used in a weight ratio of approximately 7 parts of $K_2HPO_4$ to 1 part of $KH_2PO_4$ (14.68 grams $K_2HPO_4$ and 214 grams $KH_2PO_4$ per liter to form a 100 millimole/liter solution).

The glutamate dehydrogenase is ammonia-free and is from beef liver. The lactate dehydrogenase is from beef muscle, and may be obtained, alternatively, from beef heart, hog muscle or heart, rabbit muscle, and other sources providing the enzyme which is specific for L-lactate. The diaphorase is from *Clostridium kluyveri.* The enzymes are available from various commercial sources.

The second reagent solution has a pH of about 7.4±0.1 and contains the materials set forth in Table 4 dissolved in distilled or deionized water in the proportions indicated.

Table 4

| Material | Amount Per Liter |
| --- | --- |
| Sodium alpha-ketoglutarate | 25 millimoles |
| Potassium oxalate | 53.5 millimoles |
| Sodium oxamate | 20 millimoles |
| ($K_2HPO_4$, anhydrous) ($KH_2PO_4$, anhydrous) | 100 millimoles |
| 2-p-Iodophenyl-3-p-nitrophenyl-5-phenyl tetrazolium chloride | 0.5 millimoles |

The phosphate salts are used in a weight ratio of approximately 7.8 parts of $K_2HPO_4$ to 0.7 parts of $KH_2PO_4$ (7.835 grams $K_2HPO_4$ and 0.682 grams $KH_2PO_4$ per liter to form a 100 millimoles/liter solution).

In conducting a determination, 0.5 ml. of the first reagent solution prewarmed to 37° C. and 50 microliters (ul.) of the serum undergoing test are mixed in a cuvette, and the mixture is incubated for five minutes at 37° C. At that time, 0.5 ml. of the second reagent solution prewarmed to 37° C. is added to the mixture, and the resulting mixture is incubated for fifteen minutes at 37° C. A 3 ml. quantity of 0.1 N hydrochloric acid then is added to the mixture and mixed therewith, to terminate enzymatic reaction and color formation. Absorbance at 500 nm. is read in a spectrophotometer.

The absorbance is read against a reagent blank set at zero absorbance. The activity of the transaminase in the serum sample is calculated from the absorbance obtained in the same manner with a calibrator serum having a known GOT or GPT enzyme content, but substituting the calibrator serum for the test serum in the procedure.

We claim:

1. In a method for determining glutamate oxalacetate transaminase or glutamate pyruvate transaminase present in a biological fluid, wherein L-glutamate is produced from alphaketoglutarate and an amino acid by transamination in the presence of the transaminase in the fluid, said amino acid being L-aspartate in the determination of glutamate oxalacetate transaminase and L-alanine in the determination of glutamate pyruvate transaminase, and the L-glutamate is oxidatively deaminated in a oxidation-reduction reaction with beta-nicotinamide adenine dinucleotide in the presence of glutamate dehydrogenase to produce reduced beta-nicotinamide adenine dinucleotide in an amount proportional to the content of the transaminase in the fluid, said fluid also containing an endogenous substance which reacts in an oxidation-reduction reaction with beta-nicotinamide adenine dinucleotide in the presence of glutamate dehydrogenase to produce reduced beta-nicotinamide adenine dinucleotide, thereby interfering with the determination, the improvement for obviating the interference caused by the endogenous substance which comprises:

reacting said endogenous substance present in said fluid in an oxidation-reduction reaction with beta-nicotinamide adenine dinucleotide in the presence of glutamate hydrogenase to consume the endogenous substance by conversion thereof to an oxidation product of the reaction with the production of reduced beta-nicotinamide adenine dinucleotide, reacting the resulting reduced betanicotinamide adenine dinucleotide in said fluid with pyruvate in the presence of lactate dehydrogenase to return the reduced beta-nicotinamide adenine dinucleotide to its oxidized form with the reduction of pyruvate to lactate, thereafter inhibiting the lactate dehydrogenase activity in said fluid, and thereafter producing in said fluid a quantity of L-glutamate from alpha-ketoglutarate and said amino acid by said transamination for said oxidative deamination thereof and production of reduced beta-nicotinamide adenine dinucleotide in an amount proportional to the content of said transaminase in the fluid.

2. A method as defined in claim 1 wherein said biological fluid is human blood serum.

3. A method as defined in claim 2 wherein said endogenous substance comprises an amino acid.

4. A method as defined in claim 1 wherein the lactate dehydrogenase activity is inhibited by the anions of oxamic acid and oxalic acid.

5. A method as defined in claim 1 including the additional step of reacting the reduced beta nicotinamide adenine dinucleotide product with 2-p-iodophenyl-3-p-nitrophenyl-5-phenyl tetrazolium chloride to produce the reduced form of the latter compound in an amount proportional to the content of said transaminase in the fluid.

6. A method as defined in claim 5 wherein the reaction of said additional step is conducted in the presence of diaphorase.

7. A method for determining glutamate oxalacetate transaminase present in a biological fluid, which comprises the steps of:

(1) incubating a mixture of said fluid, beta-nicotinamide adenine dinucleotide and glutamate dehydrogenase to consume by conversion to oxidation products endogenous substances present in the fluid and which react in oxidation-reduction reactions with beta-nicotinamide adenine dinucleotide in the presence of glutamate dehydrogenase with the production of reduced beta-nicotinamide adenine dinucleotide, (2) providing in the resulting mixture pyruvate and lactate dehydrogenase, and incubating the mixture to react the resulting reduced beta-nicotinamide adenine dinucleotide with the pyruvate to return the reduced beta-nicotinamide adenine dinucleotide to its oxidized form with the reduction of pyruvate to lactate, (3) inhibiting the lactate dehydrogenase enzymatic activity in the resulting mixture, and (4) providing in the resulting mixture alpha-ketoglutarate, L-aspartate, beta-nicotinamide adenine dinucleotide, and glutamate dehydrogenase, and incubating the mixture to produce L-glutamate by transamination, and oxidatively deaminate the L-glutamate and simultaneously produce reduced beta-nicotinamide adenine dinucleotide in an amount proportional to the content of said transaminase in said fluid.

8. A method as defined in claim 7 wherein said biological fluid is human blood serum and said endogenous substances include an amino acid.

9. A method as defined in claim 8 wherein in step (3), oxamate and oxalate are admixed with the resulting mixture to inhibit the lactate dehydrogenase enzymatic activity.

10. A method as defined in claim 7 including the additional step of providing in the resulting mixture diaphorase and 2-p-iodophenyl-3-p-nitrophenyl-5-phenyl tetrazolium chloride to produce the reduced form of the latter compound in an amount proportional to the content of said transaminase in said fluid.

11. A method as defined in claim 10 wherein said biological fluid is human blood serum and said endogenous substances include an amino acid, and in step (3), oxamate and oxalate are admixed with the resulting mixture to inhibit the lactate dehydrogenase enzymatic activity.

12. A method for determining glutamate pyruvate transaminase present in a biological fluid, which comprises the steps of:
(1) incubating a mixture of said fluid, beta-nicotinamide adenine dinucleotide and glutamate dehydrogenase to consume by conversion to oxidation products endogenous substances present in the fluid and which react in oxidation-reduction reactions with beta-nicotinamide adenine dinucleotide in the presence of glutamate dehydrogenase with the production of reduced beta-nicotinamide adenine dinucleotide,
(2) providing in the resulting mixture pyruvate and lactate dehydrogenase, and incubating the mixture to react the resulting reduced beta-nicotinamide adenine dinucleotide with the pyruvate to return the reduced beta-nicotinamide adenine dinucleotide to its oxidized form with the reduction of pyruvate to lactate,
(3) inhibiting the lactate dehydrogenase enzymatic activity in the resulting mixture, and
(4) providing in the resulting mixture alpha-ketoglutarate, L-alanine, beta-nicotinamide adenine dinucleotide, and glutamate dehydrogenase, and incubating the mixture to produce L-glutamate by transamination, and oxidatively deaminate the L-glutamate and simultaneously produce reduced beta-nicotinamide adenine dinucleotide in an amount proportional to the content of said transaminase in said fluid.

13. A method as defined in claim 12 wherein said biological fluid is human blood serum and said endogenous substances include an amino acid.

14. A method as defined in claim 13 wherein in step (3), oxamate and oxalate are admixed with the resulting mixture to inhibit the lactate dehydrogenase enzymatic activity.

15. A method as defined in claim 12 including the additional step of providing in the resulting mixture diaphorase and 2-p-iodophenyl-3-p-nitrophenyl-5-phenyl tetrazolium chloride to produce the reduced form of the latter compound in an amount proportional to the content of said transaminase in said fluid.

16. A method as defined in claim 15 wherein said biological fluid is human blood serum and said endogenous substances include an amino acid, and in step (3), oxamate and oxalate are admixed with the resulting mixture to inhibit the lactate dehydrogenase enzymatic activity.

17. A two-reagent assay system for determining glutamate oxalactate transaminase present in a biological fluid, which system includes a first reagent comprising beta-nicotinamide adenine dinucleotide, glutamate dehydrogenase, pyruvate, and lactate dehydrogenase, said first reagent to be admixed with said fluid initially for oxidizing endogenous substances present in the fluid so as not to interfere with the determination and then providing a product containing beta-nicotinamide adenine dinucleotide in its oxidized form, and a second reagent comprising oxamate and oxalate, said second reagent to be admixed with said product for inhibiting the enzymatic activity of said lactate dehydrogenase, and each of L-aspartate, alpha-ketoglutarate, diaphorase, and 2-p-iodophenyl-3-p-nitrophenyl-5-phenyl tetrazolium chloride included in one of said reagents, said diaphorase and said 2-p-iodophenyl-3-p-nitrophenyl-5-phenyl tetrazolium chloride being included in different reagents, for then producing the reduced form of the latter compound in an amount proportional to the content of said transaminase in said fluid.

18. A two-reagent assay system for determining glutamate oxalacetate transaminase present in a biological fluid, which system includes a first reagent comprising an aqueous solution of the following materials in the proportions indicated per liter of solution:

| Material | Amount |
| --- | --- |
| Alkali metal L-aspartate | 100–200 millimoles |
| Akali metal pyruvate | 0.25–1 millimole |
| Alkali metal adenosine-5'-diphosphate | 1–5 millimoles |
| Beta-nicotinamide adenine dinucleotide | 2–5 millimoles |
| Glutamate dehydrogenase | 40–80 I.U. $\times 10^3$ |
| Lactate dehydrogenase | 0.2–0.5 I.U. $\times 10^3$ |
| Diaphorase | 1–3 I.U. $\times 10^3$ | said first reagent to be admixed with said fluid initially for oxidizing endogenous substances present in the fluid so as not to interfere with the determination and then providing a product containing the beta-nicotinamide adenine dinucleotide in its oxidized form, and a second reagent comprising an aqueous solution of the following materials in the proportions indicated per liter of solution:

| Material | Amount |
| --- | --- |
| Alkali metal alpha-ketoglutarate | 10–50 millimoles |
| Alkali metal oxalate | 25–75 millimoles |
| Alkali metal oxamate | 10–30 millimoles |
| 2-p-Iodophenyl-3-p-nitrophenyl-5-phenyl-tetrazolium chloride | 0.2–1 millimole | each of said reagents also including 25–150 millimoles of a buffer selected from the group consisting of alkali metal phosphate, tris(hydroxymethyl)aminomethane, and N-tris(hydroxymethyl)methyl-2-aminoethanesulfonic acid, said second reagent to be admixed with said product for inhibiting the enzymatic activity of said lactate dehydrogenase and then producing the reduced form of 2-p-iodophenyl-3-p-nitrophenyl-5-phenyl tetrazolium chloride in an amount proportional to the content of said transaminase in said fluid.

19. An assay system as defined in claim 18 wherein each of said reagents has a pH of 7.3–8.

20. A two-reagent assay system for determining glutamate pyruvate transaminase present in a biological fluid, which system includes a first reagent comprising beta-nicotinamide adenine dinucleotide, glutamate dehydrogenase, pyruvate, and lactate dehydrogenase, said first reagent to be admixed with said fluid initially for oxidizing endogenous substances present in the fluid so as not to interfere with the determination and then providing a product containing beta-nicotinamide adenine dinucleotide in its oxidized form, and a second reagent comprising oxamate and oxalate, said second reagent to be admixed with said product for inhibiting the enzymatic activity of said lactate dehydrogenase, and each of L-alanine, alpha-ketoglutarate, diaphorase, and 2-p-iodophenyl-3-p-nitrophenyl-5-phenyl tetrazolium chloride included in one of said reagents, said diaphorase and said 2-p-iodophenyl-3-p-nitrophenyl-5-phenyl tetrazolium chlorie being included in different reagents, for then producing the reduced form of the latter compound in an amount proportional to the content of said transaminase in said fluid.

21. A two-reagent assay system for determining glutamate pyruvate transaminase present in a biological fluid, which system includes a first reagent comprising an aqueous solution of the following materials in the proportions indicated per liter of solution:

| Material | Amount |
| --- | --- |
| L-Alanine | 150-300 millimoles |
| Alkali metal pyruvate | 0.25-1 millimole |
| Alkali metal adenosine-5'-diphosphate | 1-5 millimoles |
| Beta-nicotinamide adenine dinucleotide | 2-5 millimoles |
| Glutamate dehydrogenase | 40-80 I.U. $\times 10^3$ |
| Lactate dehydrogenase | 0.2-0.5 I.U. $\times 10^3$ |

| -continued | |
| --- | --- |
| Material | Amount |
| Diaphorase | 1-3 I.U. $\times 10^3$ | said first reagent to be admixed with said fluid initially for oxidizing endogenous substances present in the fluid so as not to interfere with the determination and then providing a product containing the beta-nicotinamide adenine dinucleotide in its oxidized form, and a second reagent comprising an aqueous solution of the following materials in the proportions indicated per liter of solution:

| Material | Amount |
| --- | --- |
| Alkali metal alpha-ketoglutarate | 10-50 millimoles |
| Aklali metal oxalate | 25-75 millimoles |
| Alkali metal oxamate | 10-30 millimoles |
| 2-p-Iodophenyl-3-p-nitrophenyl-5-phenyl tetrazolium chloride | 0.2-1 millimole | each of said reagents also including 25-150 millimoles of a buffer selected from the group consisting of alkali metal phosphate, tris(hydroxymethyl)aminomethane, and N-tris(hydroxymethyl)methyl-2-aminoethanesulfonic acid, said second reagent to be admixed with said product for inhibiting the enzymatic activity of said lactate dehydrogenase and then producing the reduced form of 2-p-iodophenyl-3-p-nitrophenyl-5-phenyl tetrazolium chloride in an amount proportional to the content of said transaminase in said fluid.

22. An assay system as defined in claim 21 wherein each of said reagents has a pH of 7.3-8.

* * * * *